United States Patent
Bogert et al.

[11] Patent Number: 5,810,785
[45] Date of Patent: Sep. 22, 1998

[54] BLOWN-IN-PLACE BLOOD GASKET FOR A SAFETY CATHETER

[75] Inventors: David L. Bogert, Plainville; Andrew Brockway, Norfolk; David Goral, Brookfield, all of Conn.

[73] Assignee: Johnson & Johnson Medical, Inc., Arlington, Tex.

[21] Appl. No.: 699,631

[22] Filed: Aug. 19, 1996

[51] Int. Cl.⁶ ............................................. A61M 5/00
[52] U.S. Cl. ........................ 604/264; 604/264; 604/256; 604/167
[58] Field of Search .................... 604/264, 256, 604/167

[56] References Cited

U.S. PATENT DOCUMENTS 5,499,973  3/1996  Saab .......................................... 604/96
5,514,109  5/1996  Mollenauer et al. ................... 604/249
5,527,281  6/1996  Haas ........................................ 604/103

Primary Examiner—Michael Powell Buiz
Assistant Examiner—Tina Pham
Attorney, Agent, or Firm—Joseph F. Shirtz

[57] ABSTRACT

An intravenous catheter insertion devices, and in particular an extruded plastic blood sealing gasket for a blood chamber of the safety catheter. A cannula extends through the blood gasket with the assurance of a seal being present therebetween during relative sliding movement between the cannula and the blood gasket. Moreover, disclosed is a method of forming a blown-in-place extruded plastic gasket for a safety catheter adapted to slidingly receiving a cannula in sealing engagement therewith in a simple and inexpensively produced manner.

18 Claims, 4 Drawing Sheets

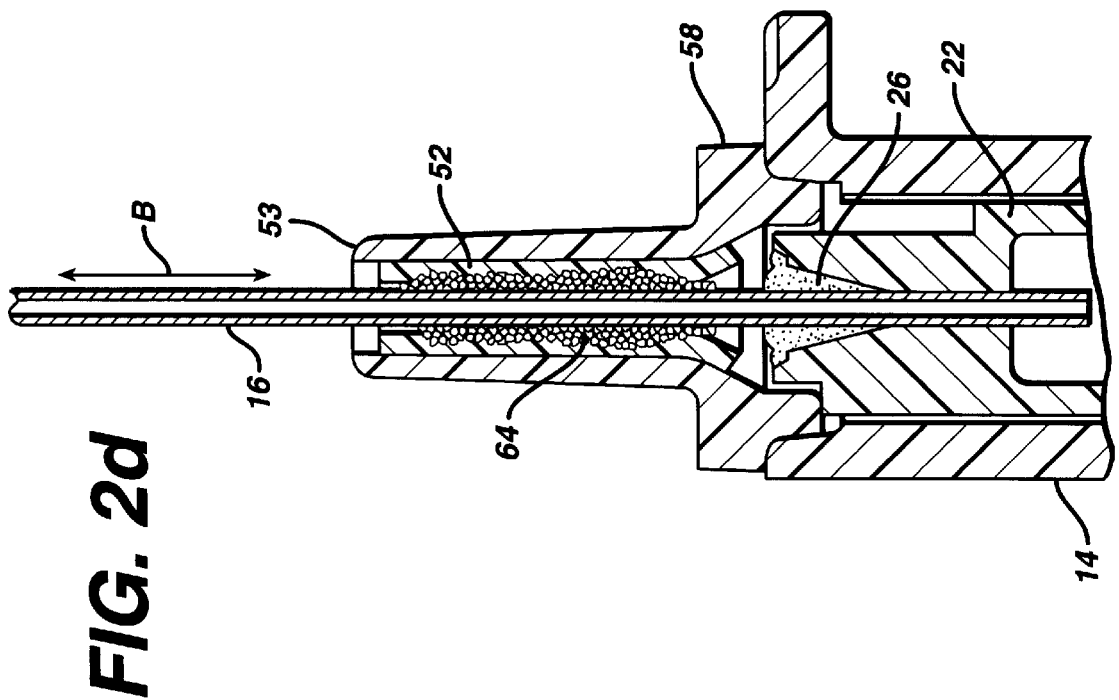
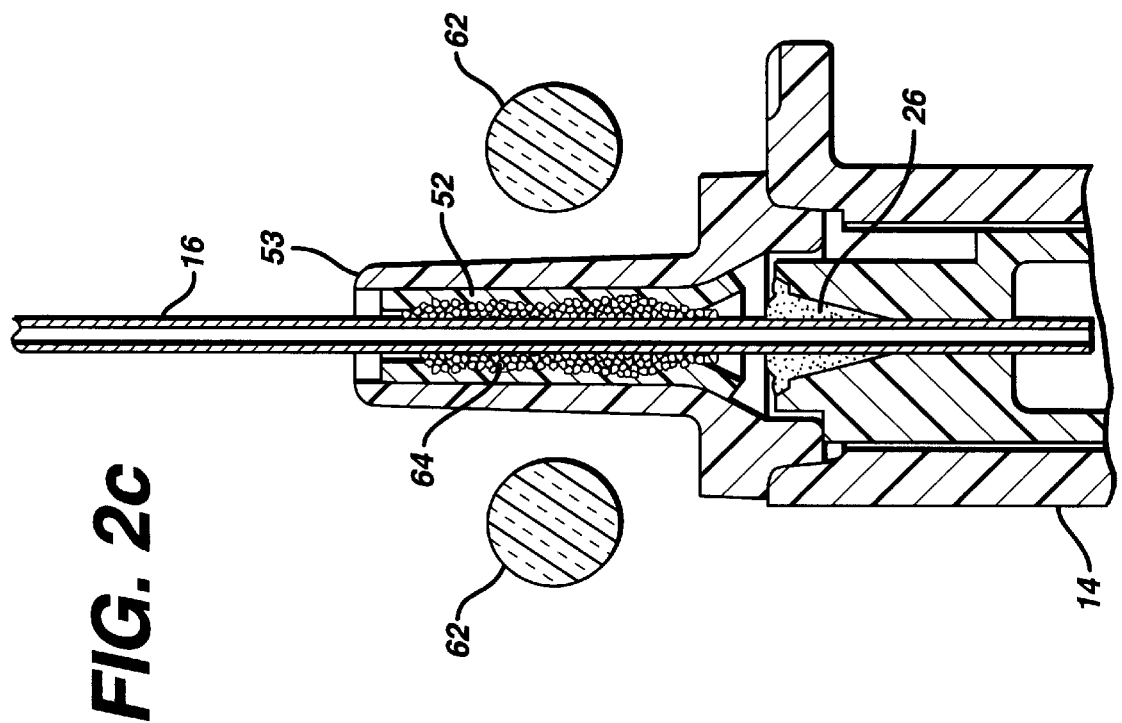
FIG. 2c
FIG. 2d

BLOWN-IN-PLACE BLOOD GASKET FOR A SAFETY CATHETER

BACKGROUND OF THE INVENTION

1. Field of the Invention

The present invention relates, in general, to intravenous catheter insertion devices, and in particular pertains to a blood gasket of a blood chamber for a safety catheter, wherein a cannula extends through the blood gasket with the assurance of a seal being present therebetween during relative sliding movement between the cannula and the blood gasket. Moreover, the invention is directed to a novel method of forming a blown-in-place gasket for a safety catheter adapted to slidingly receiving a cannula in a sealing engagement therewith in a simple and inexpensively produced manner.

Pursuant to a specific aspect of the invention the construction of various types of safety catheters necessitates the provision of a blood gasket enabling a catheter, such as in the form of a hollow steel needle, to extend therethrough so as to be slidable while sealingly engaged therein. Ordinarily, a component of the intravenous catheter insertion device, such as a nose or guard element which is mounted on a housing containing a blood chamber has a through aperture formed therein, including a recessed well through which the cannula is extended. An extrusion of plastic material arranged within the nose and extending about the cannula is positioned within the well so as to cause an inner bore surface thereof to sealingly contact the periphery of the cannula, and thereafter the cannula is exercised; in effect, axially reciprocated within the blood gasket, to ensure that it can be slidably displaced relative to the nose element of the catheter insertion device.

The utilization of clinical apparatus in which pointed hollow needles or cannulae are employed in order to puncture the skin of a patient, and especially catheters utilizing such needles to effectuate venipunctures, is well known in the medical art and is widely practiced by physicians and clinical personnel for the purpose of injecting fluids and drugs directly into the bloodstream of patients, or to withdraw blood from the patients. Additionally, during surgical operations or procedures it may be frequently required that whole blood transfusions and parenteral fluids be administered to a patient undergoing such surgical procedures. Basically, as is well known and has been employed for a considerable length of time, the introduction of such fluids into the cardiovascular systems of patients or the withdrawal of blood samples has necessitated the forming of a venipuncture utilizing a hollow rigid needle having a proximal attachment site for a fluid connection which is adapted to interconnect the needle with a source of intravenously administered fluids.

The foregoing method of administering fluids to patients through venipunctures has been subject to some rather serious problems in the administration of fluids to patients in this medical technology. Thus, a primary concern which had to be addressed resided in the inherent rigidity of the needle, the latter of which is normally generally constituted of surgical-quality steel, and while inserted into the vein of a patient, necessitated the needle to be maintained for reasons of safety in a fixed position at the general site of the venipuncture throughout the duration of fluid administration or transfusion, whereby such a procedure could conceivable consume a considerable length of time. In addition to the foregoing, at times it has been necessary to periodically draw blood samples and/or successively administer intravenous fluids to a patient, thus requiring the patient to be subjected to a series or plurality of venipunctures, each administered at a specific time and at different sites on the body, resulting in a relatively traumatic experience to the patient in view of such repeated and somewhat painful and unpleasant venipunctures.

In order to ameliorate or possibly even eliminate the foregoing problems, in the medical technology it has been more recently the practice to introduce a flexible tubular catheter of a low-friction material, such as a silastic or Teflon into the vein of a patient and to permit the catheter tube to remain in such a position over lengthier periods of time for purposes of; for example, periodically administering fluids, including parenteral fluids, blood/plasma transfusions, medications in liquid form and also for the collection of blood samples and the like. In this manner, the previously encountered trauma, extravasation, and infiltration caused by repeated venipunctures have been largely avoided, and the danger and discomfort to a patient of leaving a rigid needle in the body for a prolonged period of time has been generally overcome. Thus, in order to position the distal end of such a flexible catheter tube within the body cavity of a patient, such as a vascular cavity or vein, there is normally employed a cannula or; in essence, a hollow sharp-tipped needle for the purpose of forming the venipuncture. Thereafter, the flexible catheter tube, which is telescopically and slidably coaxially mounted on the outer circumference of the cannula or hollow needle so as to extend sleeve-like thereabout is advanced along the length of the needle into the vein subsequent to the needle having formed the venipuncture. Thereafter, the needle is adapted to be withdrawn from the interior of the catheter tube, while permitting the latter to remain within the body of the patient at the site of the venipuncture, and the needle is preferably discarded rather than being reused.

Inasmuch as the needle which has been previously positioned in the body of the patient upon forming the venipuncture may have been exposed to infectious agents; for instance, such as a patient infected with the Acquired Immune Deficiency Syndrome (AIDS) which is frequently or practically always ultimately fatal in nature, or other dangerous infectious conditions such as hepatitis, there is present the danger or hazard that the clinical personnel may inadvertently or accidentally jab or stick themselves with the used needle after withdrawal from the body of the patient, with the possibility of infection or even death resulting therefrom. Consequently, upon withdrawal of the needle from the body of the patient, the needle is generally retracted into a protective environment, such as a needle tip protective housing or structure, and safely disposed in conjunction therewith.

2. Discussion of the Prior Art

Although the utilization of blood gaskets for safety catheters or the blood chambers thereof used to collect blood samples is well known, and a method has been developed for forming in place a plastic blood gasket for a safety catheter, the currently employed method is somewhat complex and necessitates the use of either a liquid adhesive or the employment of ultraviolet curing. Thus, pursuant to a presently employed method, a cannula; in essence, the hollow steel needle or stylus component, is assembled into a plastic nose portion of the device, whereby the nose portion which is normally constituted of a molded plastic, has a central aperture for receiving the cannula so as to be slidable relative to the nose portion, and in which a well of larger diameter coaxial with the central aperture is formed in the nose portion and traversed by the cannula. Thereafter, a suitable adhesive composition is poured into the well to fill the latter, and cured through the intermediary of U.V. heat applied by ultraviolet ovens, with the cannula being exercised by being axially reciprocated so as to ensure that the cannula can be slidable relative to the nose portion of the device. This particular type of "formed-in-place gasket" necessitates either the use of a liquid adhesive and/or ultraviolet curing of the gasket material being employed, requiring extensive downtime and waste in implementing the production process.

SUMMARY OF THE INVENTION

Accordingly, in order to improve upon the currently practiced method of producing a gasket, particularly such as a blood gasket, placed into a bore of a nose portion of a catheter insertion device or safety catheter is an extruded plastic element which is of a generally hollow annular cylindrical construction, the outer diameter of the extruded element being dimensional and configured so as to prevent its being displaced out from of the nose portion. Thereafter a cannula is slipped into the nose portion and through the bore of the extrusion, with the bore being somewhat larger than the outer diameter of the cannula. One end of the cannula is adhesively fastened to a housing structure which may be a blood chamber with the other end of the cannula extending outwardly and having a sharp point or tip for insertion into the body of a patient.

The cannula is induction heated, causing the inner surface of the extrusion about its bore to foam and expand radially inwardly in response to the incorporation of an unactivated blowing agent in the plastic material of the extrusion forming the gasket. The activation temperature of the blowing agent is higher than the required extrusion melt for the extruded component, and is only activated upon induced heating being applied to the cannula at a temperature which is higher than the extrusion melt temperature. Ordinarily, prior to the heat being applied the inside or bore diameter of the extrusion for forming the blood gasket is larger by about 0.001 to 0.050 inches than the outside diameter of the cannula positioned therein and extending therethrough, such that upon the heating of the cannula to a temperature above the activation temperature of the blowing agent contained in the extrudate for the blood gasket and upon the cannula being exercised; in effect, axially reciprocated, this creates a thin pliable foam film between the cannula and the extrusion bore surfaces, thereby producing a good blood seal between the entire length of the extrusion or gasket bore and the cannula.

Release agents such as silicones or other lubricants can be incorporated in the extrusion material or coated on the inside or bore diameter of the extrusion and/or coated onto the cannula surface so as to ensure that no foam will adhere to the cannula.

Alternatively, this particular concept in the method of forming the blown-in-place blood gasket can be utilized by molding the nose portion itself with an unactivated foaming agent or a highly pressurized foam incorporated in the plastic material thereof, whereby the internal aperture or bore surface of the nose portion engages the surface of the cannula, thereby eliminating the requirement for a separate gasket-forming extrusion being positioned within the nose portion, and thereby simplifying the overall construction by reducing components.

According, it is an object to provide a novel method of forming a blown-in-place blood gasket for the cannula of a catheter insertion device.

A more specific object of the present invention is to provide method of forming blood gasket of the type described whereby an extrusion of a plastic material located within a nose portion of the catheter insertion device incorporates a foaming or blowing agent which, subsequent to the insertion of a cannula in a bore of the extrusion and heating of the cannula, causes the foaming agent in to be activated so as to create a foam forming a sealing engagement with the surface of the cannula while enabling the cannula to be axially exercised relative to the nose portion and blood gasket.

BRIEF DESCRIPTION OF THE DRAWINGS

Reference may now be had to the following detailed description of a preferred embodiment of the invention, taken in conjunction with the accompanying drawings; in which:

FIGS. 2a–2d illustrate various stages in the inventive method for forming blown-in-place blood gasket for sealingly contacting a cannula of a catheter insertion device.

DETAILED DESCRIPTION OF A PREFERRED EMBODIMENT

Figure 1A:
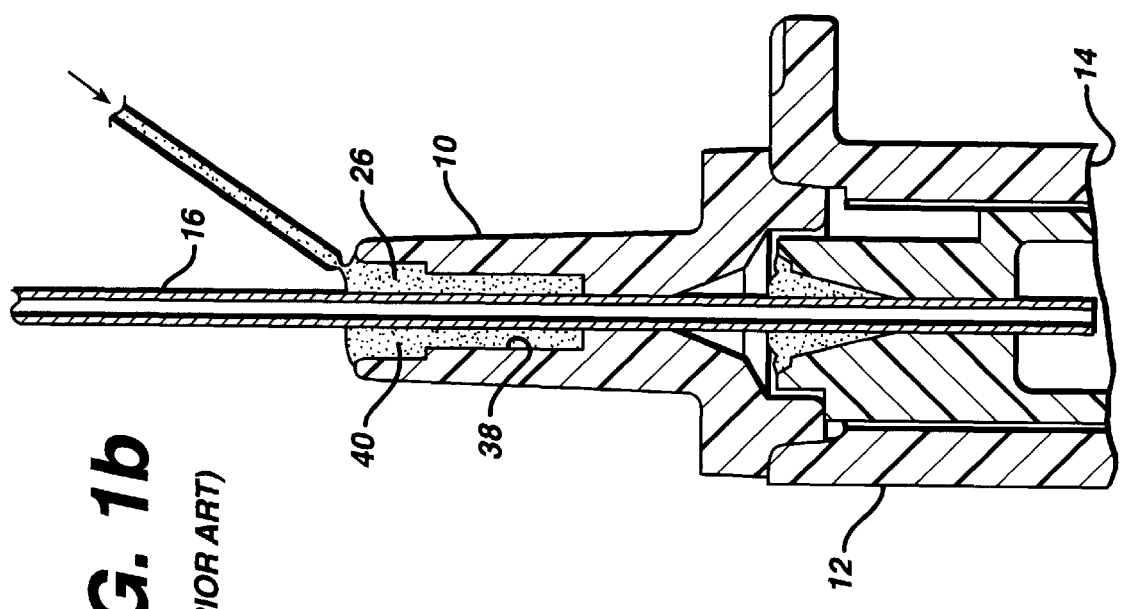
FIGS. 1a–1b illustrate various stages in the method of producing a formed-in-place blood gasket pursuant to the current state of the technology.
Figure 1B:
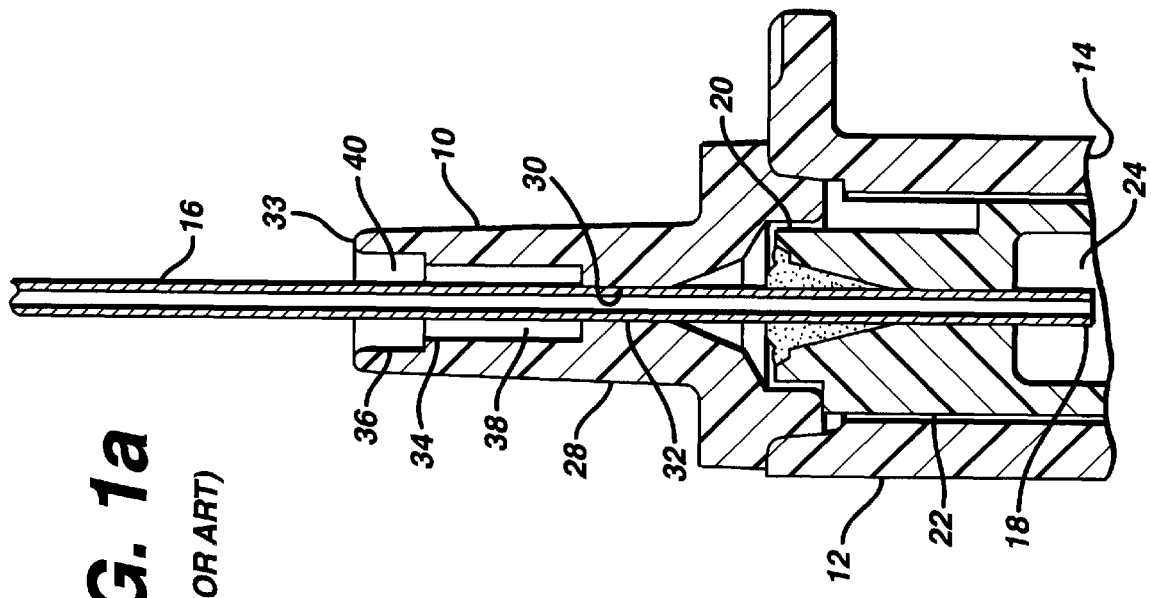

Referring now in detail to the drawings, and particularly FIGS. 1a–1b setting form a currently employed method of forming a blood gasket, illustrated in FIG. 1a is a nose portion 10 of a safety catheter (not shown) which nose portion is constituted of a generally rigid molded plastic material and which is adapted to be mounted on the front end 12 of a housing 14. A steel cannula 16 is retractable through the nose portion 10 subsequent to withdrawal of the former from the body of a patient into the housing 14 so as to protect clinical personnel or a physician from needle stick.

The rearward end 18 of the cannula 16 which extends into the housing 14 is fixedly connected to an end 20 of a blood chamber 22 so as to communicate with internal space 24 thereof, and is adapted to have an adhesive extending about the circumference of the cannula 16 so as to permanently secure the cannula 16 to the blood chamber 22 as described hereinbelow.

Figure 1C:
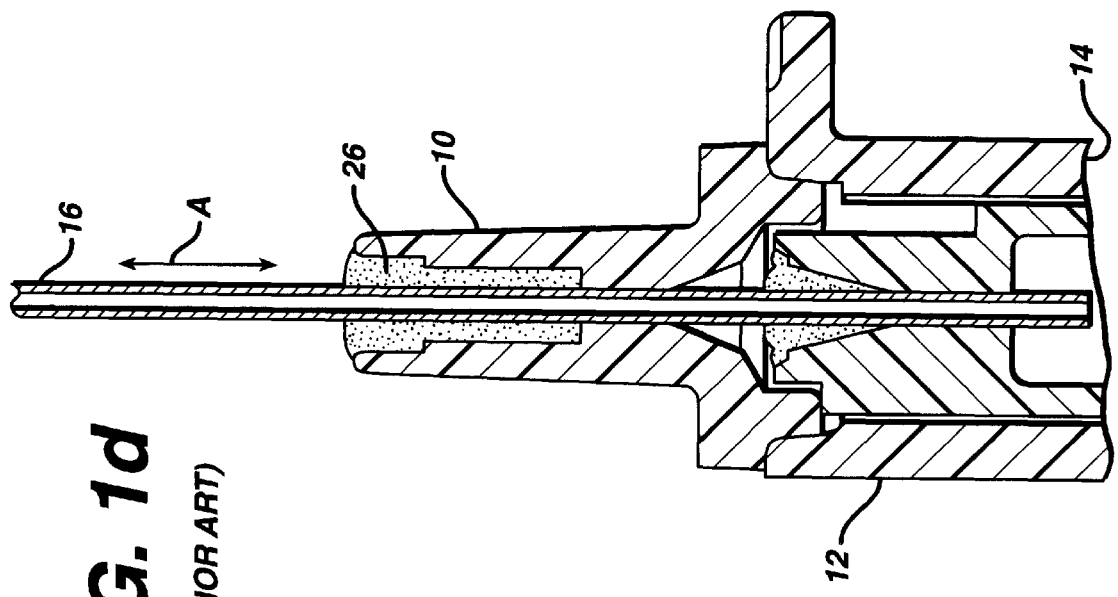
Figure 1D:
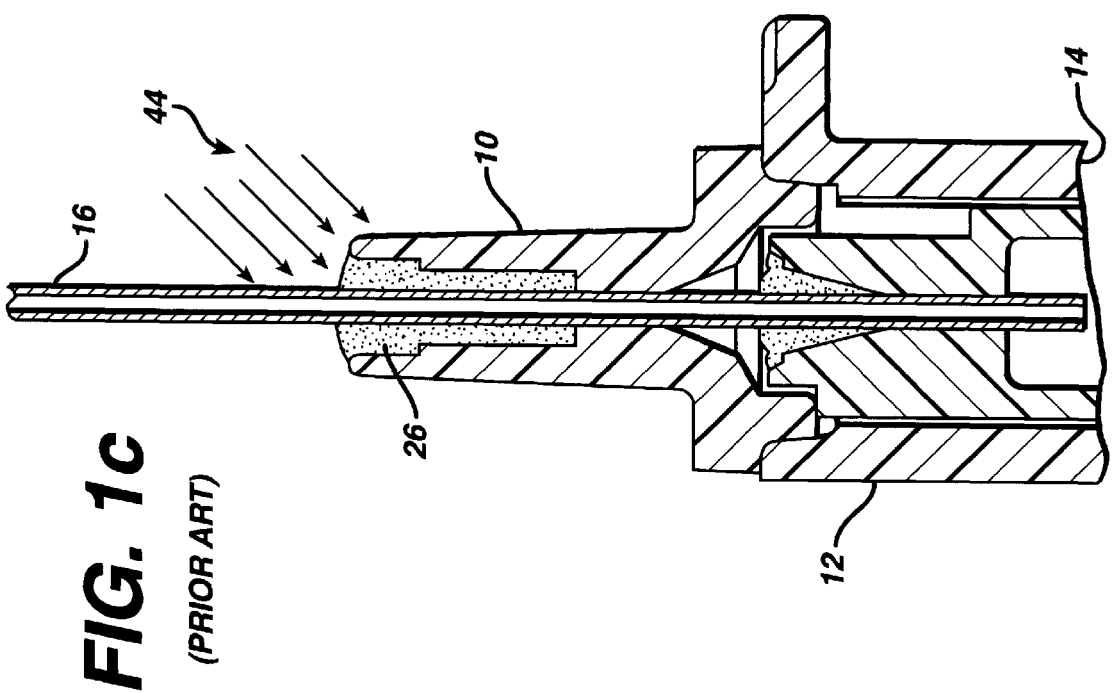

The nose portion 10 which is fixedly seated onto the leading or front end 12 of the housing 14, and which is constituted of a molded plastic element, has a generally cylindrical external configuration 28 possessing a central through aperture or bore 30 through which the cannula is extended so as to be in slidable contact with a lower portion 32 of the bore 30. The forward end 33 of the nose portion 10 has a larger diameter stepped well 34, 36 formed therein communicating with the bore portion 32 in which the cannula 16 is located, and provides an annular space 38, 40 about the cannula 16. As shown in FIG. 1b an adhesive 26 is adapted to be poured into the nose well 34, 36 so as to completely fill the space 38, 40 about the cannula 16. Thereafter, as shown in FIG. 1c, the adhesive 26 is cured by the exposure to heat produced by ultraviolet ovens 44 while the cannula 16 is exercised by being reciprocated in a longitudinal direction along its axial length, as shown by the double-headed arrow A in FIG. 1d, so as ensure that it can maintain slidability relative to the adhesive 26 while the latter still maintains a seal therewith and with the surface of well 34, 36 to which it adheres. This particular method of forming a blood gasket through the introduction and curing of adhesive 26 in the well 34, 36, which comprises either liquid adhesives and/or ultraviolet curing of settable materials requires much downtime and waste in the manufacturing process.

In order to improve upon the foregoing method in producing a blood gasket, pursuant to the present invention, as disclosed in FIGS. 2a–2d of the drawings, there is produced a so called "blown-in-place" blood gasket. In this embodiment, elements which are the same or similar to those described with regard to FIG. 1a–1b are identified by the same reference numerals and no detailed discussion thereof is deemed to be necessary for an understanding of the invention.

Figure 2B:
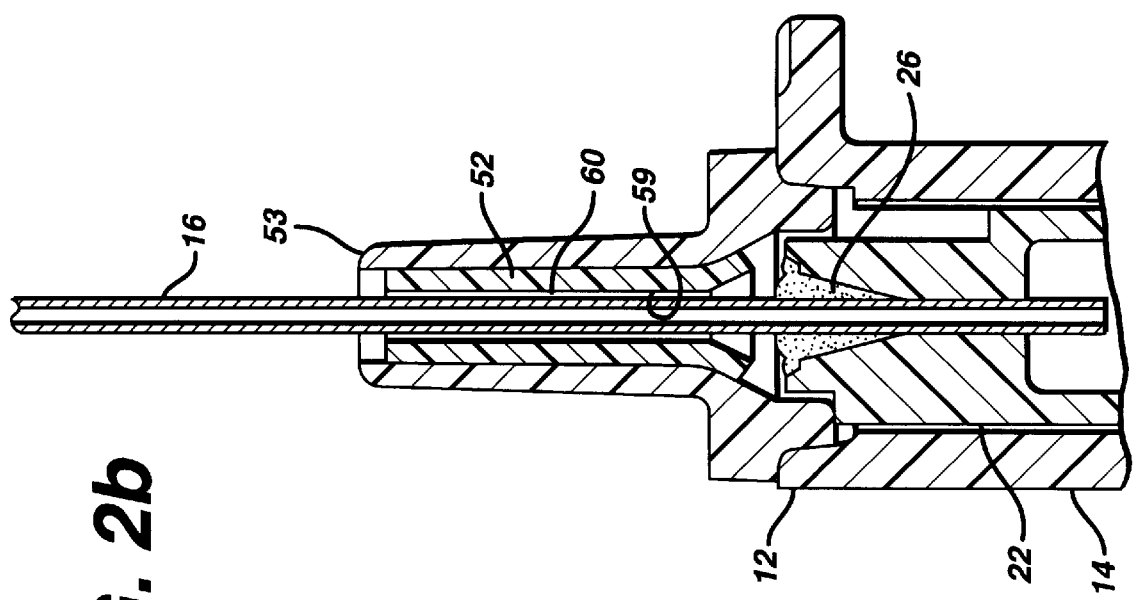
Figure 2A:
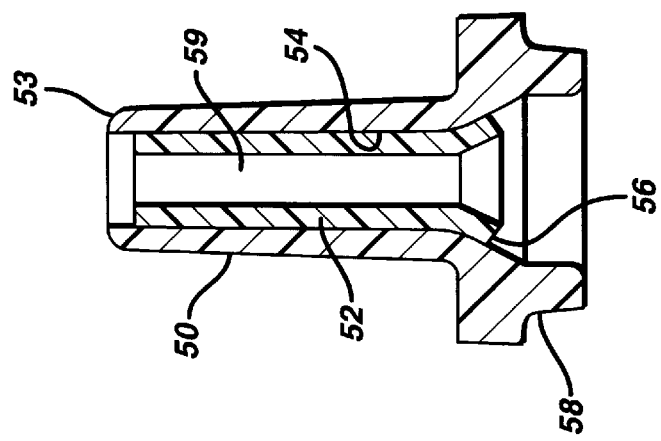

In this inventive embodiment, the nose portion 50, which is preferably also constituted of molded plastic material is of generally cylindrical shape and slightly tapers down towards the front end 53 so as to be somewhat frusto-conical. The interior of the nose portion 50 has a large-diameter through-bore 54, slightly widening towards the rear end expanding into a conical enclosure 56. The rear end 58 of the nose portion is configured similar to that of FIGS. 1a–1d and is adapted to be mounted on a housing 14 containing a blood chamber 22. Cannula 16 is fastened to the blood chamber by means of adhesive 26 and projects forwardly through the nose portion 50 as shown in FIG. 2b. A plastic extruded member 52 of generally hollow cylindrical configuration is inserted into a bore 54 of the nose portion 50. The extruded member 52 has one end towards the rear of the nose portion 50 radially outwardly chamfered or widened so as to prevent it from being displaced axially forwardly in bore 54. As shown, extruded member 52 has a longitudinal includes a central bore 59 through which the cannula 16 which is fastened at one end thereof to the blood chamber 22 can be slipped through the nose portion 50 as shown in FIG. 2b, with a circumferential space 60 being provided between cannula 16 and the wall of bore 59. The internal diameter of the bore 59 of the extruded member 52 is approximately 0.001 to 0.050 inches larger in diameter than the external diameter of the steel cannula 16. Preferably the extruded member 52 which is positioned within the nose portion 50 is constituted of a suitable plastic material which incorporates a blowing agent, the latter of which is unactivated at the extrusion melt temperature of the extruded member 52. Subsequent to the insertion of the cannula 16 through the nose portion 50 and the extruded member 52, as shown in FIG. 2b, the cannula 16 is heated, preferably by induction heating means 62, as shown in FIG. 2c, to a temperature which is higher than the activation temperature of the blowing agent and the plastic material of the extruded member 52 than that of the nose portion 50. This causes the inner or bore surface 59 of the extruded member 52 to foam and to form a sealing contact along the length thereof with the cannula 16, the latter of which is axially reciprocated or exercised along the direction of double headed arrow B so as to ensure its displacability within the foamed extruded member 52 and nose portion 50 while maintaining a suitable blood seal, the latter of which is created by means of a thin pliable foam film 64 created between the surface of the cannula 16 and the foamed bore 59 of the extruded member 52.

In order to ensure that no foam from the extruded member 52 will adhere to and potentially contaminate the surface of the cannula 16, coated on the surface of the bore 59 of the extruded member and/or coated on the cannula 16, or, alternatively incorporated into the plastic material of the extruded member 52, may be suitable release agents, such as silicones and other lubricants.

Furthermore, pursuant to a simplified modification of the invention, rather than providing an extruded member 52 within the nose portion 50, the latter can be molded from a suitable plastic material which incorporates the foaming or blowing agent, and in which the inner or bore diameter of the nose cone 50 is proximate to or slightly larger than the external diameter of the cannula 16, whereby upon the heating of the cannula 16, this will cause the bore of the nose portion to foam and sealingly close about the cannula in a manner as described hereinabove. In this instance, although the method is essentially identical to that described with regard to FIGS. 2a–2d of the drawings, there is eliminated the extruded member 52 within the nose cone 50, thereby further simplifying the construction of the safety catheter so as to render it more economical to produce.

From the foregoing, it becomes readily apparent that the present inventive method of the blowing-in-place of a blood gasket for a safety catheter is extremely simple in nature in comparison with that currently being employed in the technology and, in an inexpensive manner, produces an excellent blood seal.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A method of producing a blood sealing gasket for a safety catheter, wherein said safety catheter includes a nose portion having an elongate cannula axially slidably positioned therein, said cannula having a first end protruding from said nose portion fixedly connected with a chamber structure for receiving blood from a patient and including a second end extending from an opposite end of said nose portion for insertion into a vein of the patient; said method comprising:

(a) positioning an extruded hollow cylindrical plastic member in a central bore axially extending through said nose portion;

(b) extending said cannula through an axial bore in said hollow cylindrical plastic member, said axial bore of said hollow cylindrical plastic member for receiving said cannula being dimensioned so as to provide an annular space about said cannula;

(c) imparting heat to said cannula to cause the material of the inner surface of the axial bore of said hollow cylindrical plastic member to foam and expand radially inwardly to sealingly engage the outer surface of said cannula;

(d) and imparting axial reciprocating movement to said cannula within said foamed bore surface of the cylindrical member to inhibit binding between the cannula and said hollow cylindrical plastic member enabling axial displacement of said cannula relative to said nose portion while maintaining sealing contact with said hollow cylindrical plastic member such that the latter forms said blood sealing gasket.

2. A method as claimed in claim 1, wherein said cylindrical member is constituted of a plastic material incorporating a blowing agent having an activation temperature which is higher than the extrusion temperature for said extruded cylindrical member but lower than the temperature to which the cannula is heated.

3. A method as claimed in claim 1, wherein the inner diameter of said extruded cylindrical member prior to implementing the heating step (c) is about 0.001 to 0.050 inches larger than the outer diameter of said cannula.

4. A method as claimed in claim 1, wherein said foaming of the inner surface of said cylindrical member responsive to heating of said cannula forms a pliable foam film between said cannula and the length of the axial bore in said cylindrical member.

5. A method as claimed in claim 1, wherein said heating of the cannula comprises the application of induction heating.

6. A method as claimed in claim 1, wherein said extruded plastic material of the cylindrical member incorporates release agent means to prevent adherence of the cannula to said cylindrical member.

7. A method as claimed in claim 6, wherein said release agent means comprises a silicone.

8. A method as claimed in claim 1, wherein said cannula is coated with release agent means to prevent adherence to said cylindrical member.

9. A method as claimed in claim 8, wherein said release agent means comprises a silicone.

10. A method as claimed in claim 1, wherein said nose portion comprises a molded plastic material.

11. A method as claimed in claim 10, wherein said cylindrical member is integrally molded with said nose portion.

12. A safety catheter and blood sealing gasket, wherein said safety catheter includes a nose portion having an elongate cannula axially slidably positioned therein, said cannula having a first end protruding from said nose portion and fixedly connected with a chamber structure for receiving blood from a patient and including a second end extending from an opposite end of said nose portion for insertion into a vein of the patient; comprising (a) an extruded hollow cylindrical plastic member being positioned in a central bore axially extending through said nose portion;

(b) said cannula extending through an axial bore in said hollow cylindrical member, said axial bore in said hollow cylindrical plastic member for receiving said cannula being initially dimensioned so as to provide an annular pace about said cannula said cannula further being coated with a release agent means comprising silicone to prevent adherence to said hollow cylindrical plastic member;

(c) said cannula being subjected to heat such as that the material of the inner surface of the axial bore of said hollow cylindrical plastic member is foamed and expanded radially inwardly to sealingly engage the outer surface of said cannula; whereby said cannula is axially reciprocated within said foamed bore surface of said hollow cylindrical plastic member to inhibit binding between the cannula and cylindrical member enabling axial displacement of said cannula relative to said nose portion while maintaining sealing contact with said hollow cylindrical plastic member such that the latter forms said blood sealing gasket.

13. A gasket as claimed in claim 12, wherein said cylindrical member is constituted of a plastic material incorporating a blowing agent having an activation temperature which is higher than the extrusion temperature for said extruded cylindrical member but lower than the temperature to which the cannula is heated.

14. A gasket as claimed in claim 12, wherein the inner diameter of said extruded cylindrical member prior to being foamed is about 0.001 to 0.050 inches larger than the outer diameter of said cannula.

15. A gasket as claimed in claim 12, wherein said foaming of the inner surface of said cylindrical member responsive to heating of said cannula forms a pliable foam film between said cannula and the length of the axial bore in said cylindrical member.

16. A gasket as claimed in claim 12, wherein the cannula is heated by induction heating.

17. A gasket as claimed in claim 12, wherein said nose portion comprises a molded plastic material.

18. A gasket as claimed in claim 17, wherein said cylindrical member is integrally formed with said nose portion.

* * * * *